(12) United States Patent
Saliterman et al.

(10) Patent No.: US 11,865,357 B2
(45) Date of Patent: Jan. 9, 2024

(54) LIGHT-BASED TREATMENT DEVICES AND METHODS

(71) Applicant: Regents of the University of Minnesota, Minneapolis, MN (US)

(72) Inventors: Steven S. Saliterman, Minneapolis, MN (US); Jennifer Chmura, Minneapolis, MN (US); Brett Levac, Minneapolis, MN (US); Jerry Molitor, Minneapolis, MN (US); James Kerber, Minneapolis, MN (US); Kushal Sehgal, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 116 days.

(21) Appl. No.: 17/088,662

(22) Filed: Nov. 4, 2020

(65) Prior Publication Data

US 2021/0128940 A1    May 6, 2021

Related U.S. Application Data

(60) Provisional application No. 62/930,610, filed on Nov. 5, 2019.

(51) Int. Cl.
*A61N 5/06*     (2006.01)
*H05B 47/16*    (2020.01)
*A61F 7/00*     (2006.01)

(52) U.S. Cl.
CPC ............ *A61N 5/0616* (2013.01); *A61F 7/007* (2013.01); *H05B 47/16* (2020.01); *A61F 2007/0095* (2013.01); *A61N 2005/0626* (2013.01); *A61N 2005/0644* (2013.01); *A61N 2005/0647* (2013.01); *A61N 2005/0663* (2013.01)

(58) Field of Classification Search
CPC .......... A61N 5/0616; A61N 2005/0626; A61N 2005/0644; A61N 2005/0647; A61N 2005/0663; A61N 2005/0645; A61N 2005/0662; A61F 7/007; A61F 2007/0095; A61F 2007/0036; A61F 2007/0059;
(Continued)

(56) References Cited

U.S. PATENT DOCUMENTS 6,290,713 B1 * 9/2001 Russell ................ A61N 5/0616
                                                  607/91
2002/0138120 A1 * 9/2002 Whitehurst ............ A61N 5/062
                                                  607/88
(Continued)

OTHER PUBLICATIONS

Ash, C. et al. Effect of wavelength and beam width on penetration in light-tissue interaction using computational methods. Lasers Med Sci. 2017; 32:1909-1918.
(Continued)

*Primary Examiner* — Gary Jackson
*Assistant Examiner* — Sebastian X Lukjan
(74) *Attorney, Agent, or Firm* — Brian D. Kaul; Westman, Champlin & Koehler, P.A.

(57) ABSTRACT

A light treatment device includes a stacked structure for applying a light treatment to a patient's skin. The stacked structure includes a light source configured to emit treatment light, and a light diffusing layer. The light diffusing layer is configured to receive the emitted treatment light, diffuse the treatment light, and output diffused treatment light.

4 Claims, 8 Drawing Sheets

(58) Field of Classification Search
CPC ........ A61F 2007/006; A61F 2007/0071; A61F 2007/0096; H05B 47/16; Y02B 20/40
See application file for complete search history.

(56) References Cited

U.S. PATENT DOCUMENTS

| | | | |
|---|---|---|---|
| 2007/0208395 A1* | 9/2007 | Leclerc | A61N 5/0616 607/86 |
| 2010/0179469 A1* | 7/2010 | Hammond | A61N 5/0624 604/20 |
| 2013/0131762 A1* | 5/2013 | Oversluizen | A61N 5/0616 607/90 |
| 2013/0268034 A1* | 10/2013 | Kawase | A61N 5/0613 607/91 |
| 2015/0238774 A1* | 8/2015 | Anderson | A61K 35/04 604/20 |
| 2017/0258995 A1* | 9/2017 | Hyde | A61M 35/00 |
| 2017/0312542 A1* | 11/2017 | Palaniswamy | A61F 7/007 |
| 2019/0374792 A1* | 12/2019 | Tapper | A41D 1/002 |

OTHER PUBLICATIONS

Coffman J. Raynaud's Phenomenon. Current Treatment Options in Cardiovascular Medicine. 2000; 2:219-226.
Sicca, G. et al. Melanopsin mediates light-dependent relaxation in blood vessels. PNAS. Dec. 16, 2014; 111(50), 17977-17982.
Silva I et al. Raynaud phenomenon. Reviews in Vascular Medicine. 2016; 4-5:9-16.

\* cited by examiner

LIGHT-BASED TREATMENT DEVICES AND METHODS

CROSS-REFERENCE TO RELATED APPLICATION

The present application is based on and claims the benefit of U.S. provisional patent application Ser. No. 62/930,610, filed Nov. 5, 2019, the content of which is hereby incorporated by reference in its entirety.

FIELD

Embodiments of the present disclosure relate to devices and methods for treating Raynaud's Disease and other vascular or circulatory conditions using light with or without application of heat.

BACKGROUND

Raynaud's condition (Raynaud's Disease and Phenomenon) is a vasospastic disease characterized by episodes of reduced blood flow by vasoconstriction, commonly to the extremities including the hands and feet, but also rarely to other body parts such as the nose, ears, or lips. Episodes of vasospasms commonly occur under cold or even moderately cool temperatures, and can cause debilitating numbness and discomfort. Recurrent vasospasm episodes lead to tissue ischemia and digital ulceration, which requires intensive surgical intervention. The disease can be extremely debilitating for patients and there is a current lack of effective treatment methods.

The treatment options available for Raynaud's condition are extremely limited. Calcium channel blockers act by dilating veins and are considered the most effective treatment for Raynaud's condition, yet they are only effective in two thirds of patients and may result in serious side effects like headaches, ankle swelling, and flushing. Patients often do not comply with medication schedules for Raynaud's condition due to the negative side effects and because there are no drugs that are available for as-needed treatment.

Other treatments involve the use of devices that apply or retain heat to the affected tissues. However, these are generally bulky and inconvenient to use. Patients are unable to type on a computer when wearing these devices and find minimal relief from their use.

Treatments for such vascular conditions are needed to allow those with such conditions to lead more normal lives and provide effective point of care medicine for an otherwise disabling condition.

SUMMARY

Embodiments of the present disclosure are directed to light treatment devices for providing a light treatment to a patient, such as for treating Raynaud's and other vascular or circulatory conditions that can be shown to respond to the type of lighting, method of application and procedures described herein. One embodiment of the light treatment device includes a structure (e.g., a stacked structure) or components for applying a light treatment to a patient's skin. The structure or components include a light source configured to emit treatment light, and a light diffusing layer. The light diffusing layer is configured to receive the emitted treatment light, diffuse the treatment light, and output diffused treatment light.

Embodiments of the light treatment device may take the form of a garment that is worn by the patient. One embodiment of such a garment includes a layer of fabric material, and a structure (e.g., a stacked structure) or components supported by the layer of fabric material. The structure or components include a reflective layer, a light source configured to emit a treatment light, and a light diffusing layer. The light diffusing layer is configured to receive the emitted treatment light, diffuse the treatment light, and output diffused treatment light. The light source is positioned between the reflective layer and the light diffusing layer.

One embodiment of a light treatment device in the form of a glove includes a layer of fabric material forming the glove, at least one light source configured to emit a treatment light, and at least one fiber optic cable attached to the fabric material and configured to collect the emitted treatment light and discharge the treatment light toward the hand of a patient on which the glove is worn. In some embodiments, the glove may allow a patient's hand to be exposed to treatment light at a specific wavelength without causing excessive heating of the fingers and hands.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
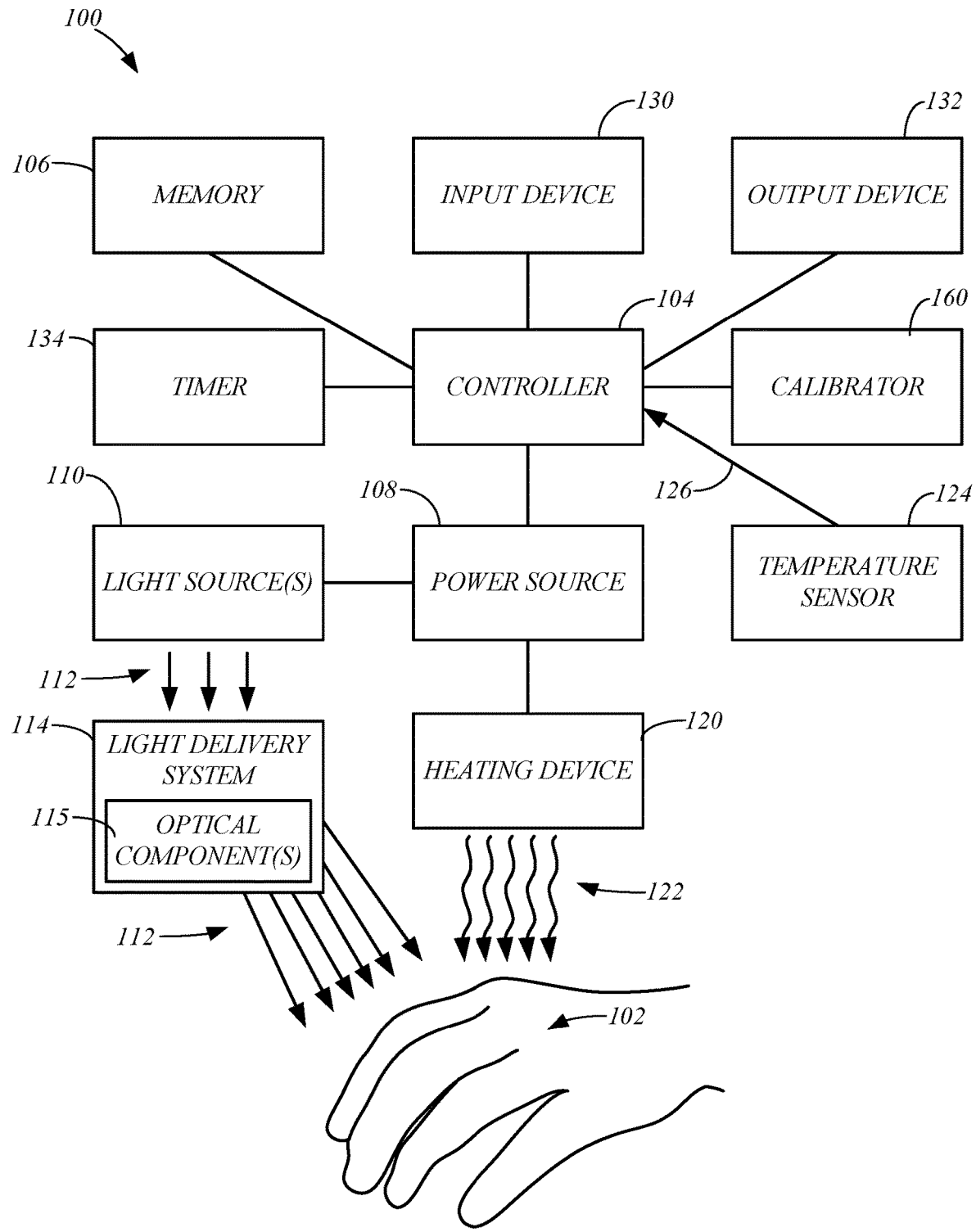
FIG. 1 is a simplified diagram of an example of a light treatment device for providing a light treatment to targeted areas of a patient, in accordance with embodiments of the present disclosure

FIG. 1 is a simplified diagram of an exemplary light treatment device 100 for providing a light treatment to targeted areas of a patient, in accordance with embodiments of the present disclosure. In some embodiments, the device 100 may also apply heat to the targeted areas to further enhance the light treatment. The light treatment with or without heat may be used to treat various conditions, such as Raynaud's condition, vascular or circulatory conditions, and/or other conditions. Embodiments of the device 100 include any suitable combination of two or more of the elements shown in FIG. 1. The device 100 may also include additional components that are not illustrated in FIG. 1.

The device 100 may be configured to apply the light to a targeted exterior area 102 of a patient, such as the hands, feet, legs, arms, torso, head, neck, etc. Thus, while the targeted area 102 is illustrated in FIG. 1 as being the skin of a hand of a patient, it is understood that embodiments of the present disclosure may include the treatment of other targeted areas of a patient, such as the patient's feet, for example.

In some embodiments, the device 100 includes a controller 104, which represents one or more processors (e.g., microprocessors) that control components of the device 100 to perform one or more functions described herein in response to the execution of instructions, which may be stored locally in memory 106 of the device 100, or in memory that is remote from the device 100. In some embodiments, the processors of the controller 104 are components of one or more computer-based systems. In some embodiments, the controller 104 includes one or more control circuits, microprocessor-based engine control systems, and/or one or more programmable hardware components, such as a field programmable gate array (FPGA), that are used to control components of the device 100 to perform one or more functions described herein. The controller 104 may also represent electrical circuits or hardware components for controlling various functions, such as a potentiometer, for example.

The device 100 may include a power source 108 for providing electrical power to components of the device 100. The controller 104 may control the power source 108 to selectively deliver electrical power to one or more components of the device 100. The power source 108 may represent a line-level power source (e.g., AC power source), a battery, or another suitable power source. When the power source 108 is in the form of a battery, the device 100 may include a conventional charging circuit for recharging the battery.

The device 100 includes a light source 110 that is configured to generate treatment light 112 for use in performing a light treatment or phototherapy on a targeted area of the patient. The light source 110 may represent multiple light sources that produce the desired light 112. The light source 110 may include any suitable light source, such as, for example, light emitting diodes (LEDs), or another suitable light source. The light source 110 may also be an array of micro-LEDs that are micro fabricated onto a sheet of material that is configured to cover and at least partially conform to the targeted area 102 (e.g., hand, foot, nose, ears, lips, etc.), such that the light treatment may be directed to the targeted area by applying the sheet over or against the targeted area.

The light source 110 may be configured to direct the treatment light 112 to the desired targeted area 102 of the patient. Alternatively, the device 100 may include a light delivery system 114 that receives the light 112 from the light source 110 and delivers or discharges the light 112 to the targeted area 102 of the patient. The light delivery system 114 may include one or more optical components 115 for capturing, transmitting, diffusing and/or discharging the light 112 to the targeted area of the patient. The optical components 115 may include, for example, mirrors, lenses, fiber optic cables, and/or other optical components.

In some embodiments, the treatment light 112 produced by the light source 110 includes light having a wavelength that is selected to provide a desired light therapy treatment to the targeted area of the patient. In one embodiment, the light 112 includes or is limited to blue light, such as light having a wavelength in the range of about 430-490 nanometers or in the range of about 430-460 nanometers. Such blue light is known to stimulate melanopsin receptors in blood vessels resulting in vasorelaxation in the targeted area. The stimulation of melanopsin receptors in blood vessels using the blue light 112 can cause vasorelaxation, which improves blood flow to the targeted area of the patient resulting in an improvement to the Raynaud's condition.

In another embodiment, the treatment light 112 includes or is limited to red light, such as light having a wavelength in the range of about 622 to 780 nanometers. Red light is known to both generate higher thermal energy than other wavelengths of visible light, as well as cause vasodilation through the endothelial nitric oxide synthase pathway. Another embodiment may have the treatment light 112 contain both blue and red light to maximize the vasorelaxation.

In some embodiments, an oral medication or topical agent may be used that contains photosensitization compounds to improve the penetration of the treatment light 112 to the targeted blood vessels, or may serve as adjuvant therapy to other treatment forms for Raynaud's condition.

The device 100 may include a heating device 120 that is configured to provide a heat treatment by applying heat to the targeted area of the patient and/or the environment surrounding the targeted area to improve the Raynaud's condition. As used herein, the heating device 120 refers to a device that is specifically configured or designed to generate heat, as opposed to an electrical component that is configured to perform a non-heating function, but produces heat as a consequence of its use, such as a light element. The heating device 120 is configured to deliver heat 122 to the targeted area of the patient through conduction, radiation, and/or convection. The heating device 120 may generate the heat using electrical heating components (e.g., resistive heating elements), chemical heating components, combustion heating components, and/or another suitable components that may be used by the heating device 120 to generate the heat.

In some embodiments, one or more temperature sensors 124 are used to detect a temperature of the targeted area (e.g., skin temperature), a temperature in the region of the targeted area, and/or a temperature of an area surrounding the targeted area, for example, and supply the controller 104 with a temperature output signal 126 that is indicative of the detected temperature. The detected temperature may be used by the controller 104 in controlling the intensity (irradiance) of the treatment light 112 and/or the duration of the treatment. Each temperature sensor 124 may take on any suitable form, such as an infrared temperature sensor, a thermocouple, a thermistor, a resistance temperature detector, a semiconductor-based temperature sensor, and/or another suitable temperature sensor. The controller 104 may use the temperature output signal or signals 126 to control the heating device 120 to provide the desired heat treatment. The one or more temperature sensors 124 may additionally provide the controller 104 with feedback for safe operation of the device 100, resulting in changes in light intensity and/or heating, and shutdown of these systems when necessary.

The device 100 may also include one or more input devices 130, which may be used to input commands to the device 100, such as the controller 104, and an output device 132 for conveying device information. Such commands may be used to control functions performed by the device 100, provide selections, navigate menus, and/or provide another input to the device 100. The input device 130 may take on any suitable form. In some embodiments, each input device 130 may include a keyboard, buttons, a mouse, input buttons, a touch panel, and/or another suitable input device.

The light treatment device 100 may also comprise data communications circuitry for communicating with an input device 130 in the form of a computing device (e.g., smartphone, laptop, etc.) that may communicate with the circuitry through a physical communications link (e.g., universal serial bus cable) or through a wireless communications link (e.g., Wi-Fi, near-field communication, Bluetooth, etc.). In this embodiment, an application for the device 100 executed on the computing device may allow a user to input commands to the device 100, and optionally perform other functions.

The device 100 may also include one or more output devices 132 for providing information or notifications to the patient or operator of the device 100. Each output device 132 may include a display, such as a monitor, for displaying information, a speaker for providing audio information, a computing device (e.g., smartphone, laptop, etc.), or another suitable output device for providing information to the patient and/or an operator of the device 100. The displayed information may provide the user of the device with instructions relating to a light and/or heat treatment performed by the device 100, for example.

In some embodiments, the device 100 includes a timer 134 that may be used to control a duration of a light and/or heat treatment performed by the device 100. The timer 134 may be manually programmed by an operator of the device 100, or controlled based upon predefined parameters of a treatment program stored in the memory 106, for example, as discussed above.

In some embodiments, the treatment performed by the device 100 includes the delivery of light 112 from the light source 110 to the targeted area of the patient either directly from the light source 110 or indirectly through the light delivery system 114. The controller 104 may control the intensity of the light 112, such as through pulse width modulation of the power supplied to the light sources 110, for example. The controller 104 may also control the duration at which the area of the patient under treatment is exposed to the light 112 to provide the desired phototherapy.

The controller 104 may also control the heating device 120 to heat the targeted area or the environment surrounding the targeted area, to provide a desired heat treatment to the targeted area of the patient. In some embodiments, the controller 104 may control the heating device 120 to control the intensity of the heat 122 generated and the duration at which the heat 122 is generated. In some embodiments, the controller 104 controls the heating device 120 based on the temperature signal 126 from the temperature sensor 124, and/or by using the timer 134.

Some treatments performed by the device 100 include the performance of both a light treatment or phototherapy and a heat treatment to the targeted area of the patient. These treatments may occur simultaneously, or alternatively, in accordance with the programmed treatment stored in the memory 106, or through control parameters (e.g., duration, light intensity, heat temperature, etc.) set by the one or more input devices 130 and/or the timer 134.

Thus, the performance of a light treatment or phototherapy in the following description includes the application of the treatment light 112 to a patient by the one or more light sources 110, and may optionally include the application of heat 122 to the patient using the heating device 120. Accordingly, the performance of a light treatment requires the use of the light source or sources 110, but does not necessarily require the presence of the heating device 120.

The inputs provided to the device 100 through, for example, the input device 130 may be used to program the device 100 to provide a desired light and/or heat therapy, for example, by programming the light source 110 to perform a light therapy defining specific parameters of the light therapy, such as a parameter defining a setting for the timer 134 to control the duration that the light source 110 is activated, a parameter defining an intensity and/or a wavelength of the light 112 output by the light source 110, parameters defining the operations of the heating device during the therapy (e.g., duration of heating controlled by the timer 134, intensity of the heat, temperature, etc.), and/or another parameter of the light therapy or treatment. The therapy program comprising one or more parameters for the light source 110 and/or the heating device 120 may be stored in the memory 106, and executed by the controller 104 to control the device 100 to perform the therapy. Thus, treatments performed by the device 100 may be manually programmed by an operator of the device 100 using the input device 130.

Alternatively, predefined treatment programs may be stored in the memory 106 and executed by the controller 104 to perform a desired light and/or heat treatment. Preprogrammed treatments may be displayed by the output device 132 and selected or modified using the input device 130. During execution of a treatment, the timer 134 may display on the output device 132, the time remaining in a current stage of the treatment, the overall time remaining in the treatment, or another time period, for example.

Figure 2:
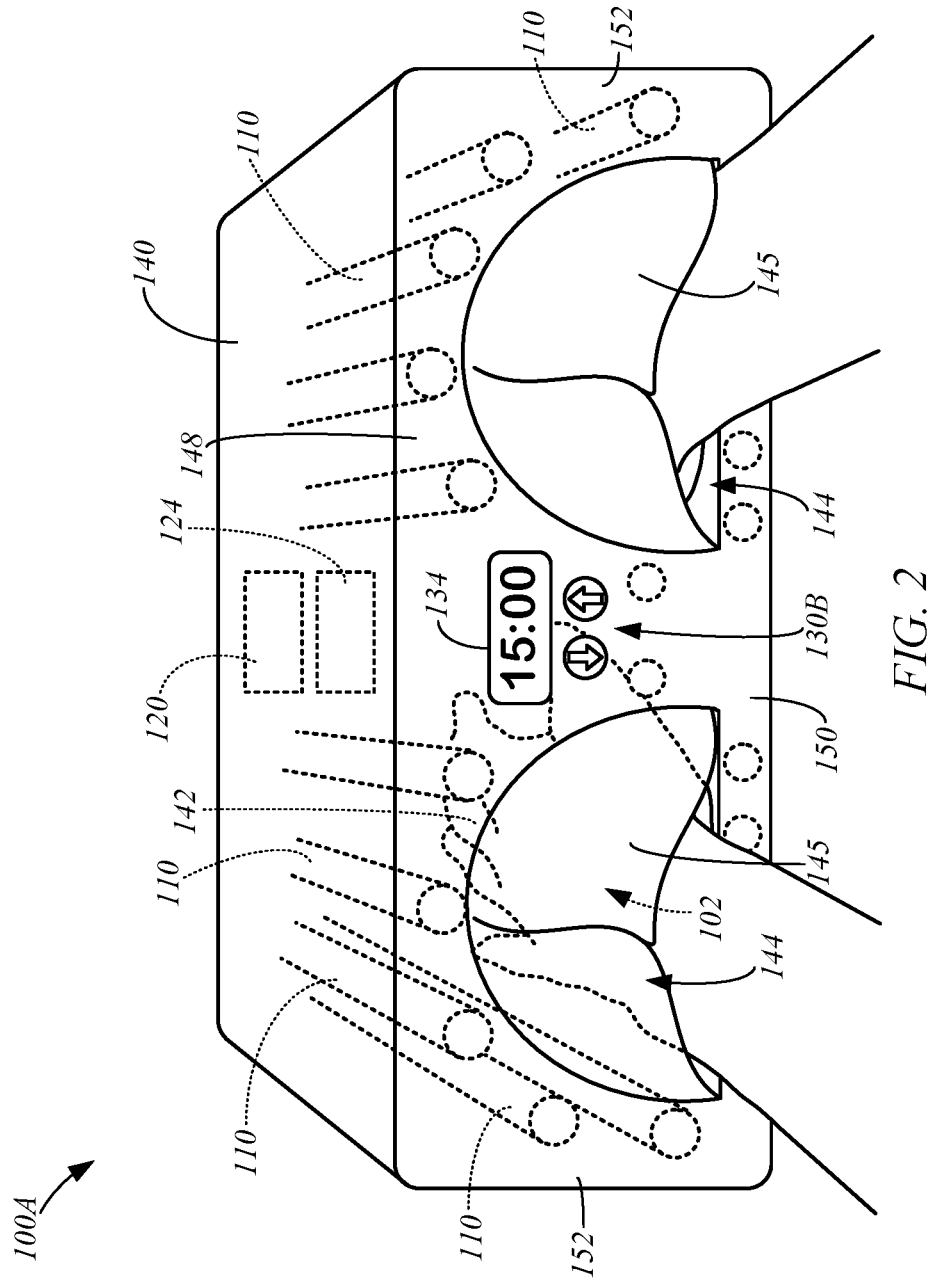
FIG. 2 is a simplified illustration of an example of stationary or desktop light treatment device, in accordance with embodiments of the present disclosure.
Figure 3A:
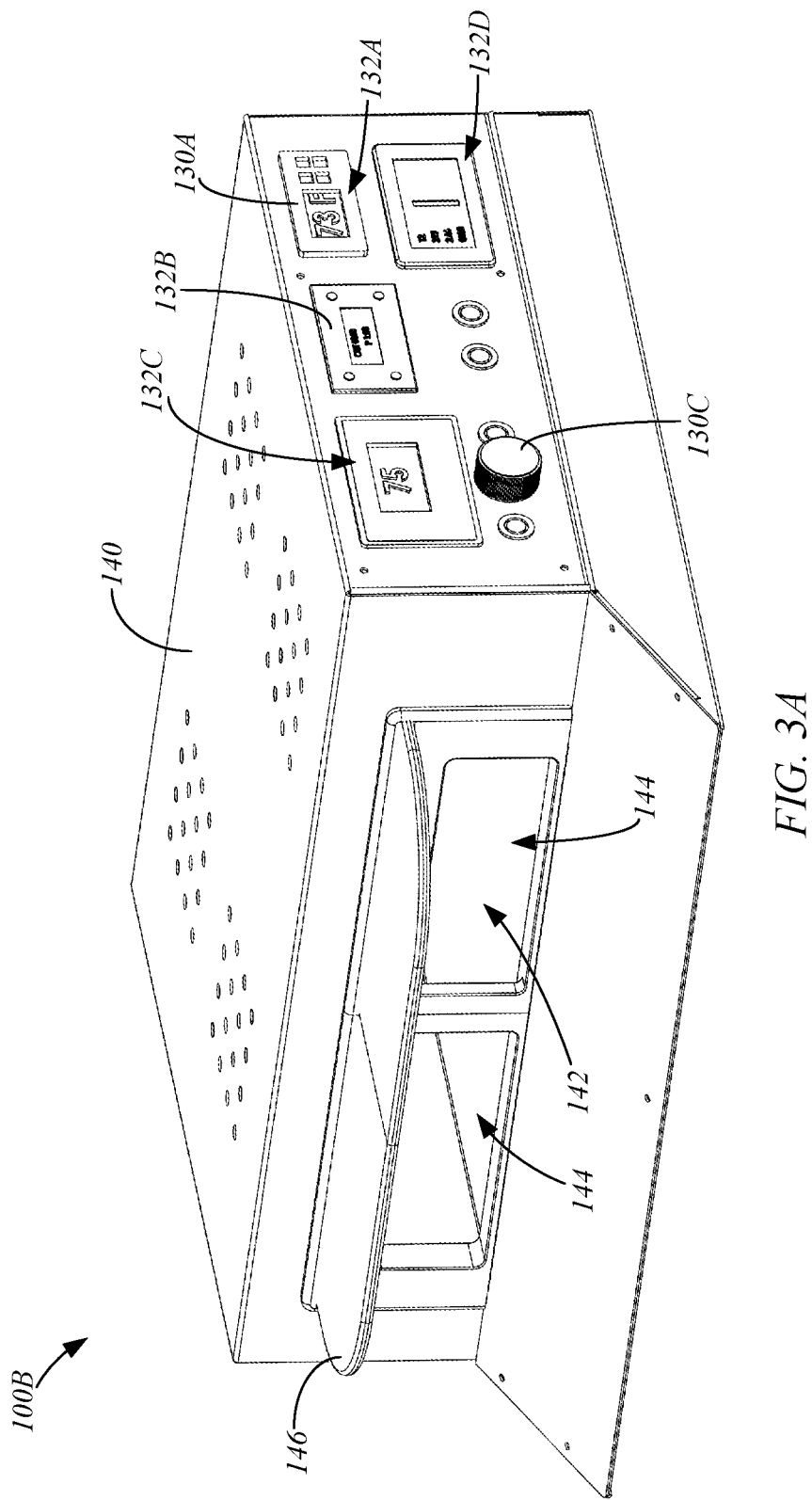
FIG. 3A is an oblique view of an example of a stationary or desktop treatment device.
Figure 3B:
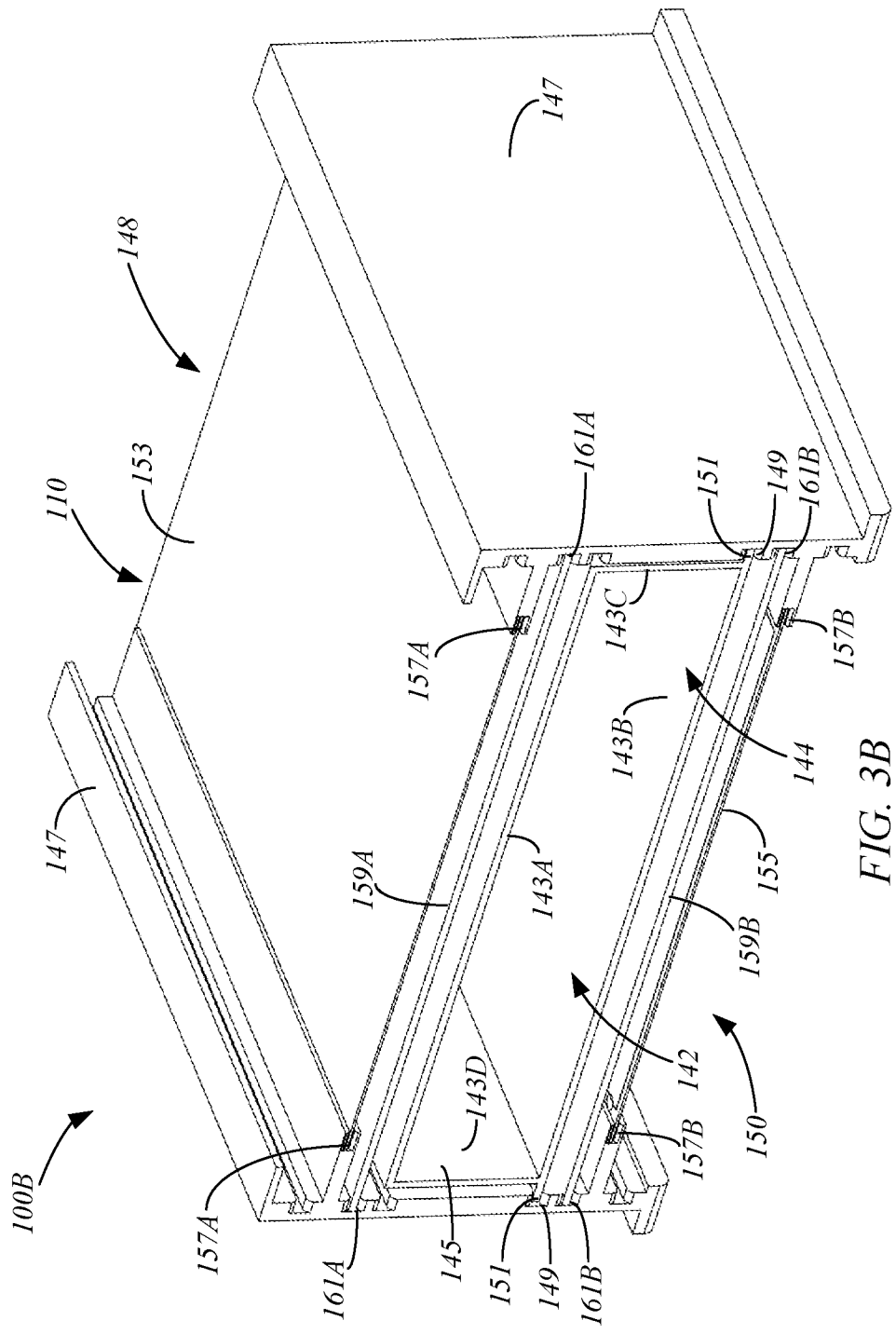
FIG. 3B is an oblique view of interior components of the device of FIG. 3A, in accordance with embodiments of the present disclosure.

In some embodiments, the device 100 may take the form of a stationary or desktop unit that performs the desired light with or without heat treatment. FIG. 2 is a simplified perspective view of an example of a stationary or desktop light treatment device 100A, FIG. 3A is an oblique view of an example of a stationary or desktop treatment device 100B, and FIG. 3B is an oblique view of interior components of the device 100B, in accordance with embodiments of the present disclosure. While the devices 100A and 100B may include all or a subset of the components described above with reference to FIG. 1, only a limited number of the components are shown in FIGS. 2 and 3A-B in order to simplify the illustrations.

In some embodiments, the light treatment devices 100A and 100B each include a housing 140 that defines an interior cavity 142 that receives a portion of the patient that is configured to receive the light therapy. In some embodiments, the housing 140 includes one or more openings 144 through which the desired portion of the patient may be inserted into the cavity 142. In the example devices 100A and 100B, the openings 144 are configured to allow a patient to extend their hands into the interior cavity for treatment, as shown in FIG. 2. It is understood that the housing 140, the cavity 142 and the openings 144 may be adjusted to accommodate a different portion of a patient, such as the patient's feet, for example.

The interior cavity 142 may be defined by clear walls through which a light treatment may be transmitted, as well as opaque walls to block the transmission of light from reaching portions of the cavity 142 or components of the device. The interior walls may be formed of glass, plexiglass, or another suitable material. The interior cavity may also be made of acrylic material (e.g., Acrylite® Santinice light diffusion acrylic) with imbedded reflective beads serving to simultaneously diffuse the light while supporting the hands of the patient and isolating from them the instrument interior.

For example, as illustrated in FIG. 3B, the interior cavity 142 may be defined by a top wall 143A and a bottom wall 143B formed of a clear or light diffusing material. Sidewalls 143C and 143D may also be included. In some embodiments, the walls 143A-D are integrated into a single unit 145. A frame 147 of the device 100B may be configured with slots 149 that are configured to receive corresponding tabs 151 of the unit 145, or the walls 143A and 143B.

Some embodiments of the devices 100A and 100B include features to prevent or limit the amount of the treatment light that escapes from the devices, such as through the openings 144, to reduce undesired patient exposure to the treatment light. For example, the openings 144 may include a flexible drape 145 (FIG. 2) or a suitable alternative to prevent treatment light and/or heat from escaping from the interior cavity 142 while in use. A hood 146 may also be used to block treatment light escaping through the openings 144, as shown in FIG. 3. During use, the patient may wear suitable light attenuating or blocking goggles or eyewear (e.g., Honeywell Ultra-Spec 2000 UVEX safety eyewear) and/or coverings to prevent undesired exposure to the treatment light 112 escaping through the openings.

One or more of the light sources 110, such as LEDs, are contained within the housing, such as within or around the interior cavity 142, and are arranged to provide the desired exposure of the targeted area. For the treatment of a patient's hands, the light sources 110 may be distributed across an upper region 148 of the housing 140 to expose a top portion of the patient's hands that are received in the cavity 142, across a lower region 150 of the housing 140 and below the patient's hands to expose the underside of the patient's hands within the cavity 142, and/or to the sides 152 of the patient's hands within the cavity 142, as indicated in FIG. 2. A similar configuration may be used to treat the feet of a patient, one or both arms of a patient, one or both legs of a patient, a torso of a patient, or another area of the patient.

As illustrated in FIG. 3B, embodiments of the example device 100B include one or more light sources 110, which may be in the form of an upper LED panel 153 positioned above the top wall 143A in the upper region 148, and/or a lower LED panel 155 positioned below the bottom wall 143B in the lower region 150. In some embodiments, the frame 147 includes slots 157A that receive and support the upper LED panel 153, and/or slots 157B that receive the lower LED panel 155.

In some embodiments, the device 100B includes an upper light diffuser 159A and/or a lower light diffuser 159B, such as when the top and bottom walls 143A and 143B are formed of a clear material rather than a light diffusing material. The light diffusers 159 operate as components of the light delivery system 114 (FIG. 1) to diffuse the treatment light 112 emitted by the LED panels 153, and more evenly distribute the treatment light over the targeted area of the patient within the interior cavity 142. The light diffusers 159 may include any suitable conventional light diffusing material. The frame 147 may receive and support the diffusers 159 via slots 161A and 161B. Accordingly, the device 100B utilizes a stacked structure of the one or more light sources 110 and diffusers 159 to facilitate the application of treatment light 112 to a targeted area of a patient.

The stationary or desktop devices 100A and 100B may also include a heating device 120, as indicated in FIG. 2. The heating device 120 may be configured to directly heat the targeted area of the patient (e.g., the patient's hands) and/or heat the interior cavity 142 to a desired temperature. The devices 100A and 100B may also include fans to assist in controlling the temperature within the cavity 142. The controller 104 may use the temperature sensor 124 to control the heating device 120 and fans (if present) and the heat treatment of the targeted area of the patient.

The stationary or desktop devices 100A and 100B may include one or more input devices 130 for setting various treatment parameters. For example, the devices 100A and 100B may include an input device 130 in the form of a temperature control panel 130A (FIG. 3) that may be used to set the desired temperature of the interior cavity 142, or an input device in the form of a timer input device 130B (e.g., buttons) (FIG. 2), which may be used to set a timing parameter for a timer 134 that controls a duration of treatments performed by the device 100A. Additionally, a light intensity input device 130C (FIG. 3), such as a dial, may be used to control an intensity parameter (e.g., irradiance level $(mW/m^2)$) of the light treatment to which the patient's hands or other body part is exposed.

Output devices 132 may be used to display various information relating to components of the devices 100A and 100B and/or a light treatment performed by the devices. For example, the output devices 132 may include: a temperature output device 132A (FIG. 3) that displays a current temperature based on a temperature signal 126 from a temperature sensor 124 or a temperature setting used to control the heating device 120; a timer output device 132B (FIGS. 2 and 3), such as a display, indicating a current time remaining in a light treatment and/or a timer setting for a light treatment; a light intensity or irradiance level output device 132C (FIG. 3), such as a display, indicating a power level of the light treatment; and/or a power monitor output device 132D (FIG. 3), such as a display, indicating various power level readings, such as the voltage and current being supplied to the light sources 110.

In some embodiments, the light treatment device 100 includes a calibrator 160, as indicated in FIG. 1. The calibrator 160 allows a technician to calibrate the light intensity or irradiance level setting, such as that set by the input device 130C of the device 100B, with power supplied by the power source 108. This calibration generally involves mapping power supplied to the light sources 110 by the power source 108 to corresponding light intensity or irradiance levels of the treatment light 112 discharged into the cavity 142 by the light sources 110. Thus, the mapping may be formed by sensing the light intensity or irradiance level within the cavity 142 for a variety of power level setting. The light intensity or irradiance level of the treatment light 112 within the cavity 142 may be measured using a suitable spectrometer, such as the UPRtek MK35ON Premium Spectrometer, for example. When the calibration is complete, the mapping may be used to identify a setting of the light intensity or irradiance level input device 130C (FIG. 3) for a desired irradiance level of the treatment light 112.

Figure 4:
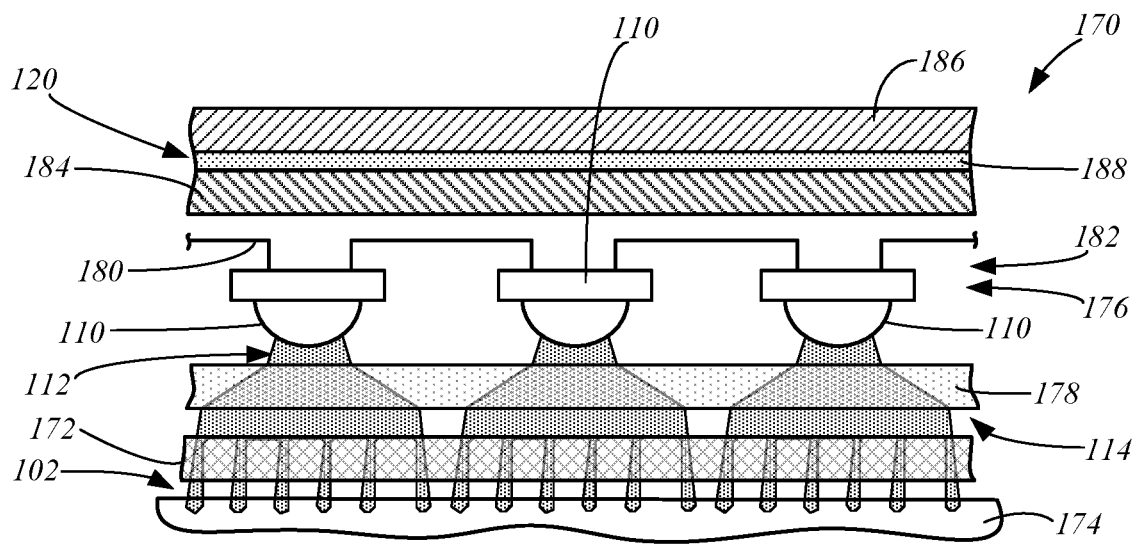
FIG. 4 is a simplified cross-sectional view of an exemplary stacked or multilayered structure that may be used to form a portion of a light treatment device, in accordance with embodiments of the present disclosure.

FIG. 4 is a simplified cross-sectional view of an exemplary stacked or multilayered structure 170 that may be used to form a portion of a light treatment device, in accordance with embodiments of the present disclosure. The multilayered structure 170 is generally configured to be positioned on or near the targeted area that is configured to receive the treatment. Components used to complete a device 100 using the structure 170, such as the controller 104, the power source 108, and other components are not shown in order to simplify the illustration.

In some embodiments, the multilayered structure 170 includes a material or fabric layer 172 that is configured to contact the skin 174 of the targeted area 102 of the patient. The layer 172 may comprise silk, nylon, polyester, or other suitable material. The material or fabric layer 172 may also be formed of or include a material that conforms to the skin and has optical properties for emitting light at the required wavelength, as well as the ability to dissipate heat.

The multi-layered structure 170 may also include one or more light sources 110, such as LEDs, in a layer 176. Each of the light sources 110 is configured to direct treatment light 112 through the layer 172 and to the skin 174 of the patient. In some embodiments, the structure 170 includes a light diffusing layer 178 that forms a portion of a light delivery system 114 for delivering the light 112 from the light sources 110 to the skin 174 of the patient. The light diffusing layer 178 may include any suitable conventional light diffusing material, such as plastics or fabrics, for example. The light sources 110 may be connected through suitable wiring 180, which may be encased in polydimethylsiloxane (PDMS) or other suitable material, in a layer 182. The light sources 110 and/or the components forming the light delivery system 114 may be derived by microfabrication of the components on or in the material or fabric layer 172, or another layer of the structure 170.

The multilayered structure 170 may also include a reflective layer 184 that is configured to direct the light 112 generated by the light sources 110 toward the skin 174 of a patient and trap the light 112 between the layer 184 and the skin 174. Exemplary embodiments of the reflective layer 184 include mylar or other suitable reflective material.

The multi-layered structure 170 may also include a layer 186 that may be formed of cloth or other suitable material. In some embodiments, the layer 186 comprises a thermally insulative material to trap heat within the multi-layered structure 170 for heating the skin 174 of the patient. The layer 186 may also operate to block the light 112 from escaping into the external environment. The layer 186 may also limit or control the amount of heat produced, and assist in removing unwanted heat (by conductive and convective means), thereby assuring comfort and safety.

In some embodiments, the structure 170 includes a heating device 120 in the form of a heating layer 188. Exemplary embodiments of the heating layer 188 include resistive heating elements interwoven within the material of the layer 188, for example. In one alternative, heating elements may be interwoven within the layer 172 to position the heating device 120 closer to the targeted area of the patient.

The multi-layered structure 170 may be positioned against or near the skin 174 of the patient to provide a desired light and/or heat treatment to the skin 174 of the patient. The light treatment may be performed by the controller 104 (FIG. 1) activating the light sources 110 to deliver treatment light 112 to the skin 174, such as through the light diffusing layer 178, which operates to diffuse the received light 112. That is, the diffusing layer 178 operates to spread out the received light 112 and increase the area covered by the emitted light 112, as indicated in FIG. 4. A passive heat treatment may be performed by thermally insulating the targeted area 102 using the multi-layered structure 170, such as the insulative layer 186. When the structure 170 includes the heating layer 188, the controller 104 may perform an active heat treatment by generating heat adjacent the targeted area 102 using the heating layer 188.

Figure 5:
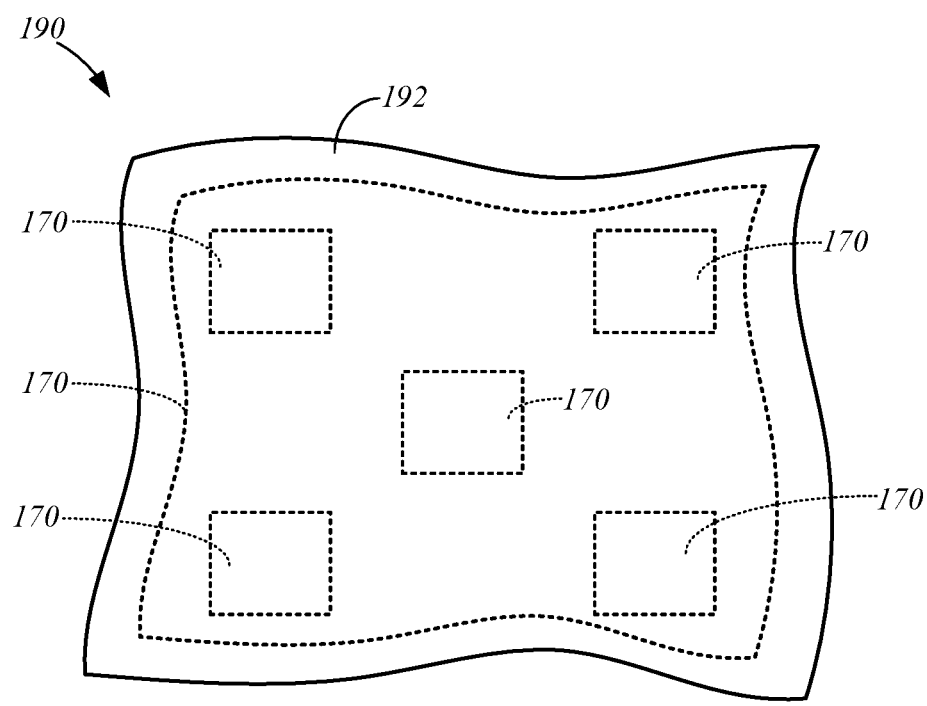
FIG. 5 is an example of a pad or blanket light treatment device, in accordance with embodiments of the present disclosure.

The structure 170 may be incorporated within a pad or blanket 190 to form a light treatment device, an example of which is provided in the simplified illustration of FIG. 5. The pad or blanket may be configured to lay against the targeted area of a patient and may partially conform to the targeted area, during application of the treatment light 112 (FIG. 4) to the targeted area. Material 192 (e.g., fabric) forming the pad or blanket may be substantially or entirely formed by the structure 170, or include one or more portions that include the structure 170, as illustrated in phantom lines. The fabric layer 186 (FIG. 4) of the structure 170 may extend beyond other layers of the structure 170 and used as the material 192.

Figure 6A:
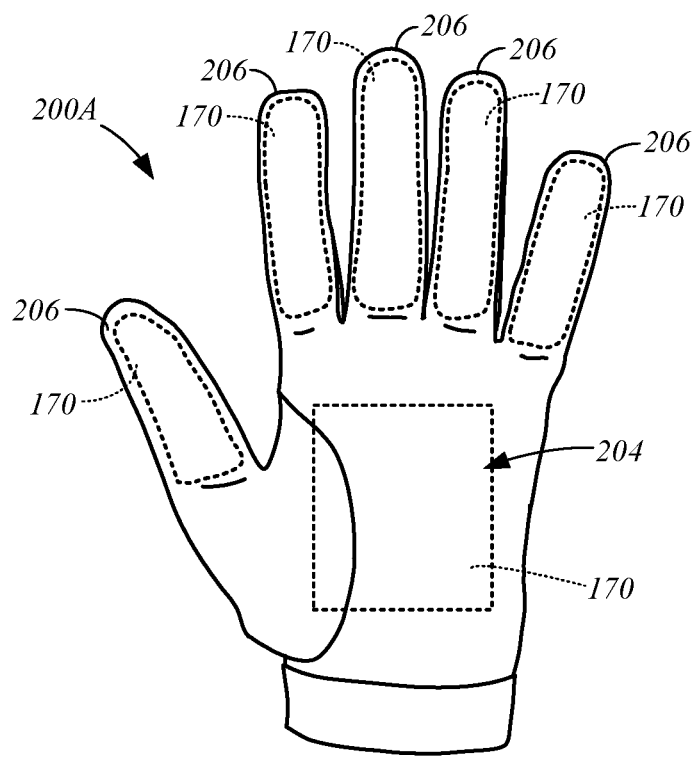
FIGS. 6A-D illustrate various examples of garments configured to be worn by a patient that include a light treatment device, structure or material, in accordance with embodiments of the present disclosure.

FIGS. 6A-D illustrate various examples of garments 200 configured to be worn by a patient that include the structure or material 170, in accordance with embodiments of the present disclosure. FIG. 6A is a simplified illustration of an example of a glove 200A that includes the structure 170, in accordance with embodiments of the present disclosure. The material forming the glove 200A may include the structure 170 for applying a light treatment over substantially all of the wearer's hand, or one or more portions of the material forming the glove 200A may include the structure 170 for applying a light treatment to targeted areas of the wearer's hand. For example, a central portion 204 of the glove may include the structure 170 on the palm side and/or the back side of the glove for delivering a light therapy to the palm and/or back side of the wearer's hand. In another embodiment, one or more finger portions 206 of the glove may include the structure 170 for delivering a light therapy to the corresponding fingers of the wearer.

Figure 6B:
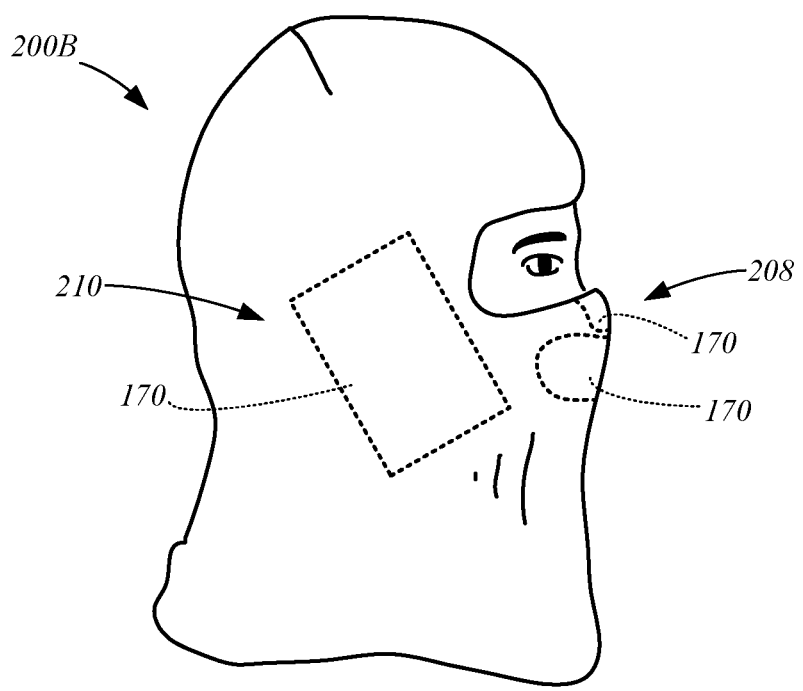

FIG. 6B is a simplified illustration of an example of a head covering 200B that includes the structure 170, in accordance with embodiments of the present disclosure. The material forming the head covering 200B may include the structure 170 for applying a light treatment over substantially all of the wearer's head, or one or more portions of the material forming the head covering may include the structure 170 for applying a light treatment to targeted areas of the wearer's head. For example, the material forming the head covering 200B may include a facial portion 208 configured to cover the nose and/or mouth of the wearer that includes the structure 170 for applying a light treatment to the nose and/or mouth of the wearer. The head covering 200B may also include a portion 210 configured to cover the ears and/or cheeks of the wearer that includes the structure 170 for applying a light treatment to the ears and/or cheeks of the wearer.

The head covering 200B may be configured to support the particular structure or structures 170 that are used. For example, when the head covering 200B includes structures 170 only in the facial portion 208, the head covering 200B may take the form of a conventional facial mask, rather than the substantially full head covering shown in FIG. 6B.

Figure 6C:
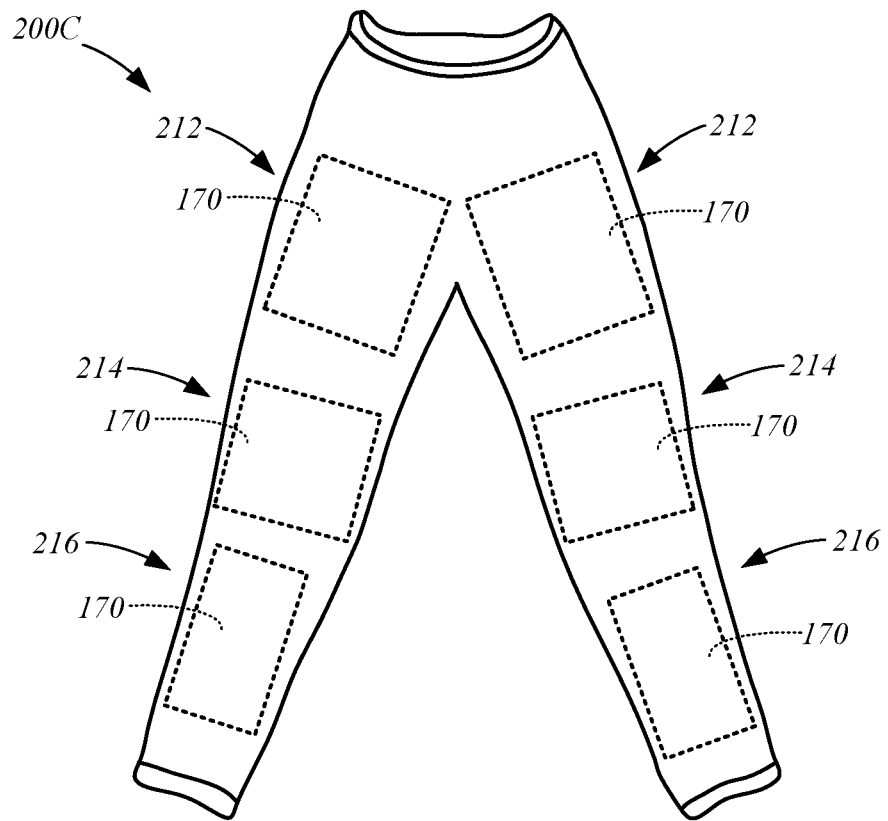

FIG. 6C is a simplified illustration of an example of a pair of pants 200C that includes the structure 170, in accordance with embodiments of the present disclosure. The material forming the pants may include the structure 170 for applying a light treatment over substantially all of the wearer's legs, or one or more portions of the material forming the pants may include the structure 170 for applying a light treatment to targeted areas of the wearer's legs. For example, an upper leg portion 212, a central leg portion 214, and/or a lower leg portion 216 of the pants 200B may include the structure 170 for applying a light treatment to those portions of the legs of the wearer.

Figure 6D:
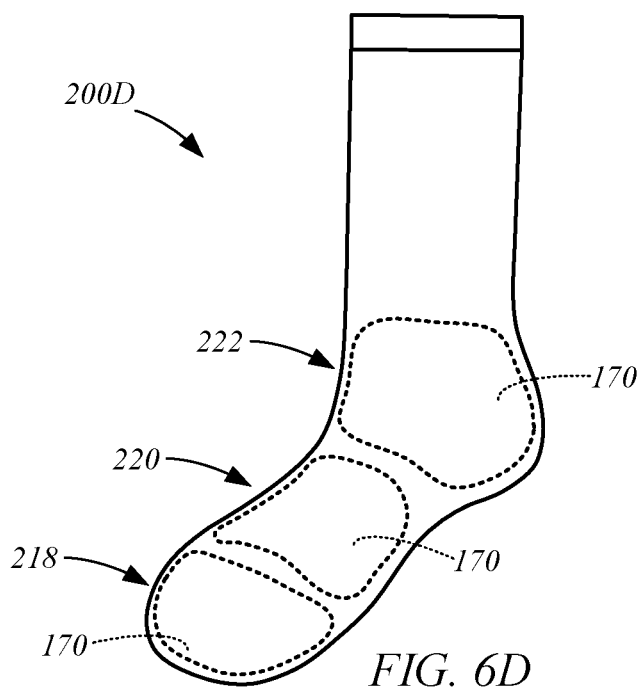

FIG. 6D is a simplified illustration of an example of a sock 200D that includes the structure 170, in accordance with embodiments of the present disclosure. The material forming the sock may include the structure 170 for applying a light treatment over substantially all of the wearer's foot and ankle, or one or more portions of the material forming the sock may include the structure 170 for applying a light treatment to targeted areas of the wearer's foot or ankle. For example, a toes portion 218, a middle foot portion 220, and/or an ankle portion 222 of the sock may include the structure 170 for applying a light treatment to those portions of the foot/ankle of the wearer.

Figure 7:
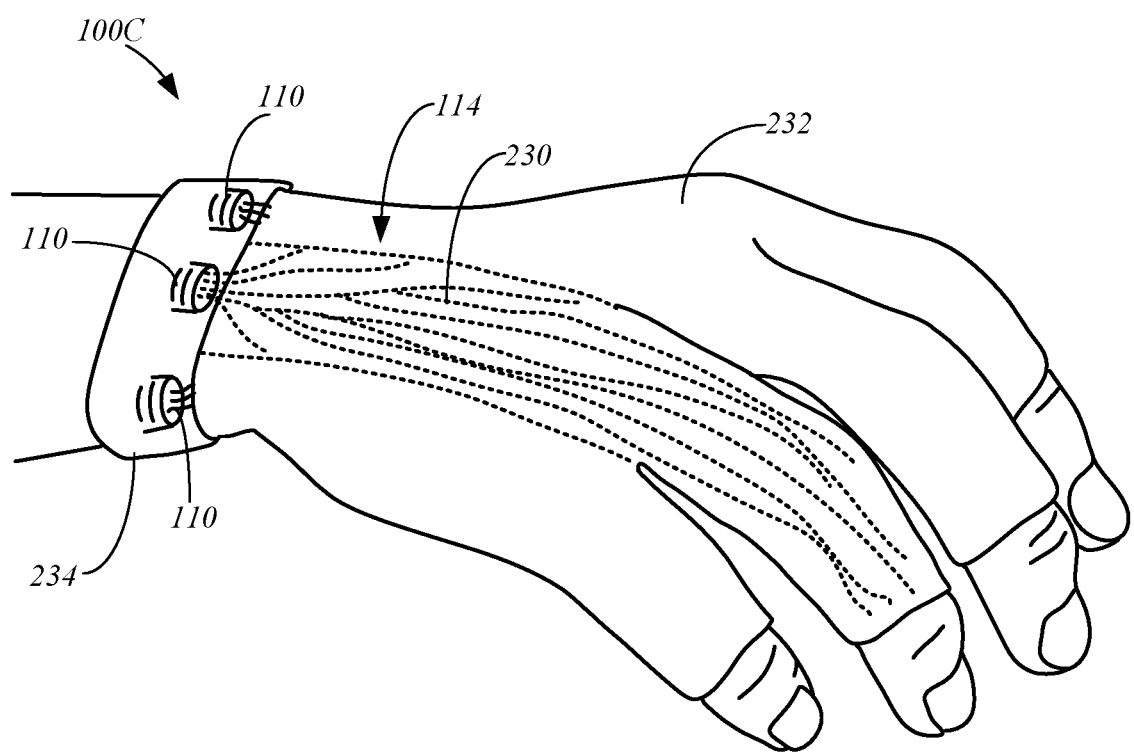
FIG. 7 is a simplified isometric view of an exemplary light treatment device, in accordance with embodiments of the present disclosure.

FIG. 7 is a simplified isometric view of an exemplary light treatment device 100C, in accordance with embodiments of the present disclosure. In some embodiments, the device 100C includes light sources 110 and a light delivery system 114 comprising a plurality of fiber optic cables 230 that are interwoven within a material 232. The fiberoptic cables 170 operate to deliver the light 112 generated by the light sources 110 along the material 172, and direct the light 112 through or from the material 172 to the targeted area of the patient. The material 232 with the interwoven fiberoptic cables 230 may be used to form at least portions of gloves as shown in the example of FIG. 7, or at least portions of other items, such as pads, blankets and garments (shirts, pants, hats, socks, etc.), to allow for the treatment of a desired targeted area of a patient.

In some embodiments, the heating device 120 may be incorporated within the material 232 or as a layer of the material 232, such as illustrated by the heating layer 188 of the structure 170, to provide a heat treatment to a desired targeted area of the patient. For example, resistive heating elements forming the heating device 120 may be interwoven within the material 232, or provided in a layer of the material 232 to provide heat to the targeted areas of the patient.

In some embodiments, the device 100C includes a base portion 234 that contains the light sources 110. The base portion 234 may also include other components of the device 100C, such as the controller 104, the power source 108 (e.g., battery), a universal serial bus (USB) charger, the temperature sensor 124, one or more input devices 130 (e.g., on/off switch), and/or other components. In the glove example of the device 100C shown in FIG. 7, the base portion 234 may take the form of a bracelet that may be worn on the wrist of the patient. The fiberoptic cables 230 may be configured to deliver the treatment light 112 to targeted areas of the patient's hand through corresponding sections of the glove. Thus, the light 112 may be delivered to the skin of the fingers, the back of the hand, the palm of the hand, and/or another targeted area using the fiberoptic cables 230. In some embodiments, the material 232 does not extend to the tips of the patient's fingers, as shown in FIG. 7.

Additional embodiments of the present disclosure are directed to applying a light treatment to a targeted area of a patient using the devices 100 and the structure 170 described above. For example, embodiments of these light treatments may involve exposing the targeted area of the patient to the treatment light 112 using one of the devices 100 (e.g., one of the devices 100A-C), the structure 170, and/or a device comprising the structure 170 (e.g., the pad or blanket 190, garment 200, etc.). The treatment may be controlled by parameters that control a duration that the treatment light 112 is generated, an intensity of the treatment light 112, a temperature of the targeted area or an environment in which the targeted area is located, a wavelength of the light treatment, and/or other parameters, as discussed above.

Although the embodiments of the present disclosure have been described with reference to preferred embodiments, workers skilled in the art will recognize that changes may be made in form and detail without departing from the spirit and scope of the present disclosure.

What is claimed is:

1. A light treatment device for applying a light treatment to a patient's skin, the device comprising a stacked structure including:
   a light source configured to emit treatment light; and
   a light diffusing layer configured to receive the emitted treatment light, diffuse the treatment light, and output diffused treatment light,
   wherein:
   the treatment light has a wavelength within a range of 430-490 nanometers;
   the light treatment device further comprising:
     a housing containing the stacked structure and including an interior cavity into which the diffused treatment light is projected, and at least one opening, through which a portion of the patient may be extended into the interior cavity;
     a controller configured to control the light source to adjust an intensity of the emitted treatment light based on a light intensity parameter;
     a light intensity input device configured to set the light intensity parameter, wherein a user may adjust the light intensity parameter using the light intensity input device;
     a light intensity output device configured to display information indicative of the light intensity parameter;
     a timer;
     a timer output device configured to display time information;
     a heating device configured to convert electrical energy into heat and heat the interior cavity;
     a temperature sensor having a temperature output that is indicative of a temperature within the interior cavity;
     a temperature input device configured to set a temperature setting; and
     a temperature output device configured to display at least one of the temperature setting and a temperature indicated by the temperature output;
     the controller is configured to control the heating device based upon the temperature output and the temperature setting; and
     the controller is configured to control a duration that the light source emits the treatment light using the timer, and the time information is indicative of the duration.

2. The device of claim 1, further comprising at least one of:
   one or more flexible drapes configured to cover gaps between the at least one opening and the patient during use; and
   a hood extending from an exterior of the housing and configured to form a barrier between the at least one opening and a portion of the patient that is exterior to the interior cavity and block at least a portion of the light escaping from the interior cavity.

3. The device of claim 1, wherein the at least one opening in the housing includes a pair of hand openings, wherein each of the patient's hands may extend into the interior cavity through one of the hand openings.

4. The device of claim 1, wherein the stacked structure is attached to a layer of fabric material, and the diffused treatment light is transmitted through the layer of fabric material.

* * * * *